(12) United States Patent
Piironen et al.

(10) Patent No.: US 11,046,590 B2
(45) Date of Patent: Jun. 29, 2021

(54) METHOD AND AN APPARATUS FOR MONITORING AND CONTROLLING DEPOSIT FORMATION

(71) Applicant: KEMIRA OYJ, Helsinki (FI)

(72) Inventors: Marjatta Piironen, Oulu (FI); Iiris Joensuu, Espoo (FI); Mehrdad Hesampour, Espoo (FI); Jaakko Ekman, Vantaa (FI)

(73) Assignee: KEMIRA OYJ, Helsinki (FI)

( * ) Notice: Subject to any disclaimer, the term of this patent is extended or adjusted under 35 U.S.C. 154(b) by 0 days.

(21) Appl. No.: 16/065,515

(22) PCT Filed: Dec. 22, 2016

(86) PCT No.: PCT/FI2016/050907
§ 371 (c)(1),
(2) Date: Jun. 22, 2018

(87) PCT Pub. No.: WO2017/109287
PCT Pub. Date: Jun. 29, 2017

(65) Prior Publication Data
US 2019/0002304 A1  Jan. 3, 2019

(30) Foreign Application Priority Data
Dec. 23, 2015  (FI) ...................................... 20156009

(51) Int. Cl.
*C02F 1/00* (2006.01)
*G01N 21/64* (2006.01)
(Continued)

(52) U.S. Cl.
CPC .............. *C02F 1/008* (2013.01); *C02F 1/441* (2013.01); *C02F 1/442* (2013.01); *C02F 1/444* (2013.01);
(Continued)

(58) Field of Classification Search
None
See application file for complete search history.

(56) References Cited

U.S. PATENT DOCUMENTS 7,910,004 B2   3/2011   Cohen et al.
8,160,305 B2   4/2012   Laurint et al.
(Continued)

FOREIGN PATENT DOCUMENTS

CN   101384342 A   3/2009
CN   101910515 A   12/2010
(Continued)

OTHER PUBLICATIONS

Seok-Tae Kang, et al., "Direct observation of biofouling in crossflow microfiltration: mechanisms of deposition and release", Journal of Membrane Science, 2004, pp. 151-165, vol. 244.
(Continued)

*Primary Examiner* — Richard C Gurtowski
(74) *Attorney, Agent, or Firm* — Buchanan Ingersoll & Rooney PC

(57) ABSTRACT

A method and apparatus for monitoring deposit formation in a process having an aqueous flow is provided. According to exemplary embodiments, a feed flow of an aqueous liquid is provided onto a receiving surface to be monitored. At least part of a receiving surface is illuminated with at least one light source. Visual data is collected across the receiving surface and analyzed. The quality and type of deposition attached to the receiving surface is classified based on information obtained from the analyzed visual data, and a quantitative scaling and/or fouling indication is computed based on the classification.

28 Claims, 8 Drawing Sheets

(51) Int. Cl.
| | |
|---|---|
| *G01N 21/85* | (2006.01) |
| *G01N 21/94* | (2006.01) |
| *C02F 1/44* | (2006.01) |
| *C02F 1/52* | (2006.01) |
| *G06K 9/20* | (2006.01) |
| *G01N 17/00* | (2006.01) |
| *C12M 1/34* | (2006.01) |
| *G06K 9/03* | (2006.01) |
| *C12M 1/00* | (2006.01) |
| *G06K 9/62* | (2006.01) |
| *C02F 103/02* | (2006.01) |
| *C02F 103/10* | (2006.01) |
| *C02F 103/28* | (2006.01) |
| *C02F 103/08* | (2006.01) |

(52) U.S. Cl.
CPC .......... *C02F 1/5209* (2013.01); *C02F 1/5281* (2013.01); *C12M 1/3476* (2013.01); *C12M 31/02* (2013.01); *G01N 17/008* (2013.01); *G01N 21/6428* (2013.01); *G01N 21/6456* (2013.01); *G01N 21/6486* (2013.01); *G01N 21/85* (2013.01); *G01N 21/94* (2013.01); *G06K 9/036* (2013.01); *G06K 9/2018* (2013.01); *G06K 9/628* (2013.01); *C02F 1/004* (2013.01); *C02F 2103/023* (2013.01); *C02F 2103/08* (2013.01); *C02F 2103/10* (2013.01); *C02F 2103/28* (2013.01); *C02F 2209/00* (2013.01); *C02F 2209/005* (2013.01); *C02F 2303/20* (2013.01); *C02F 2303/22* (2013.01); *G01N 2021/6439* (2013.01); *G06K 2209/19* (2013.01)

(56) References Cited

U.S. PATENT DOCUMENTS

| | | | |
|---|---|---|---|
| 9,280,726 | B2 | 3/2016 | Dorris et al. |
| 10,451,605 | B2 | 10/2019 | Hietaniemi |
| 2006/0175256 | A1* | 8/2006 | Masten .................. B01D 61/04 210/638 |
| 2009/0045144 | A1* | 2/2009 | Cohen .................. B01D 61/025 210/745 |
| 2009/0141963 | A1 | 6/2009 | Laurint et al. |
| 2010/0261255 | A1* | 10/2010 | Pereira ..................... C01D 3/14 435/252.1 |
| 2011/0067737 | A1* | 3/2011 | Sun ........................ B01D 61/18 134/34 |
| 2012/0258547 | A1 | 10/2012 | Von Drasek et al. |
| 2013/0120556 | A1 | 5/2013 | Dorris et al. |
| 2013/0220922 | A1 | 8/2013 | Joensuu et al. |
| 2013/0335731 | A1* | 12/2013 | Jorden ............... G01N 15/0227 356/73 |
| 2014/0000346 | A1* | 1/2014 | Hoek .................. B01D 61/025 73/38 |
| 2014/0293040 | A1 | 10/2014 | Hietaniemi |
| 2015/0001151 | A1 | 1/2015 | Nakano et al. |
| 2015/0291993 | A1 | 10/2015 | Vela et al. |

FOREIGN PATENT DOCUMENTS

| | | |
|---|---|---|
| CN | 102741683 A | 10/2012 |
| CN | 104081200 A | 10/2014 |
| EP | 2 609 990 A1 | 7/2013 |
| JP | 2009524521 A | 7/2009 |
| JP | 2013223835 A | 10/2013 |
| JP | 2015009174 A | 1/2015 |
| WO | WO 2007/087578 A2 | 8/2007 |
| WO | WO 2011/163278 A2 | 12/2011 |
| ZA | 2002/1809 B | 10/2002 |

OTHER PUBLICATIONS

Michal Uchymiak, et al., "A novel RO ex situ scale observation detector (EXSOD) for mineral scale characterization and early detection", Journal of Membrane Science, 2007, pp. 86-95, vol. 291.

Finnish Search Report of Finnish Patent Application No. 20156009, dated Jun. 20, 2016.

International Search Report (PCT/ISA/210) dated Apr. 3, 2017, by the European Patent Office as the International Searching Authority for International Application No. PCT/FI2016/050907.

Written Opinion (PCT/ISA/237) dated Apr. 3, 2017, by the European Patent Office as the International Searching Authority for International Application No. PCT/FI2016/050907.

Office Action dated Jul. 25, 2019, by the Japanese Patent Office in corresponding Japanese Patent Application No. 2018-532678, and an English Translation of the Office Action. (11 pages).

Notification of the First Office Action dated Mar. 30, 2020, by the Chinese Patent Office in corresponding Chinese Patent Application No. 201680075506.6, and an English Translation of the Office Action. (17 pages).

* cited by examiner

In the beginning, no fouling

After one week, fouling exists

METHOD AND AN APPARATUS FOR MONITORING AND CONTROLLING DEPOSIT FORMATION

FIELD OF THE INVENTION

The present invention relates to a method and an apparatus for detecting, monitoring and controlling deposit formation on wetted surfaces. More specifically, the invention is directed to the detection and classification of scaling and fouling in water-intensive processes, based on collected visual data from surfaces in process plants or from dedicated monitoring cells.

BACKGROUND OF THE INVENTION

Increasing global need for water and wastewater treatment is driving the development of large-scale membrane filtration processes. In particular, water desalination via reverse osmosis (RO) technology provides a solution to the world's water shortage problem providing millions of cubic meter of fresh water from seawater per day. Higher quality, as well as supply of filter membranes, has together with environmental demands made membrane processes, such as microfiltration (MF), ultrafiltration (UF), nanofiltration (NF) membranes and reverse osmosis (RO) attractive processes to complement or replace conventional systems and sedimentation processes to remove particles, organic matter and dissolved salt.

Membrane filters are being used in both wastewater treatment to e.g. replace settling of activated sludge processes, and in low/high-salinity water where reverse osmosis with MF and UF pre-treatment as a replacement for conventional granulated or sand filters applied for removing salt from water.

However, the success of membrane and reverse osmosis technology is challenged by the fouling problem. Fouling decreases the permeate flow through the membrane, and is recognized as the main problem in the application of membrane filtration technologies. Several types of membrane fouling exist: including inorganic fouling or scaling, colloidal fouling, organic fouling, and biofouling.

A particular problem is biofouling, where biological material development forms a sticky layer on the membrane surface. Biofouling refers to the deposition, growth and metabolism of bacteria cells or flocs on the membranes. Biofouling leads to higher energy input requirement as an effect of increased biofilm resistance and osmotic pressure, lower quality of product water due to increased solutes accumulation on the membrane surface, and thus to significant increase in both operating and maintenance costs.

Paper mills do have problems with deposit formation on the surfaces as well. fouling can occur on the surfaces of water feed pipes, water tanks, splash areas of paper machine wet end or on any metal surfaces in the wet part of a paper machine. Deposits in paper mill are often organic and may consist of pitch, white pitch, or stickies, or the deposits may be inorganic or consist of biofouling.

Such depositions, when allowed to grow, will release undesired particles of organic, inorganic and biofouling deposits to the papermaking process and may lead to end product defects or breakages in the paper web.

In mining industry, where water is also much used as a flow and transport medium, depositions may occur on metal surfaces and causing problems e.g. in sieves, filters and membranes used in the process.

Various measures are known in the art to clean and monitor affected surfaces and membranes. It is well known to add chemicals to the feed water, in order to reduce or eliminate scaling and fouling, and an important aspect of e.g. large scale filtration is to monitor the build-up of scaling and fouling on the equipment. See EP 2609990, for example. Correct timing and optimization of service and cleaning activities is an important cost factor, and a good monitoring system is also a basis for research around the phenomenon leading to the deposition and agglomeration of various matter, and for control purposes, e.g. for timing and addition of chemicals to the water feed.

Definitions

Reverse Osmosis (RO) Process

Reverse osmosis is a modification of the natural process known as osmosis, wherein of two solutions with different dissolved salt concentrations, water flows from the less concentrated solution to the more concentrated solution through a semipermeable membrane. In reverse osmosis, the flow direction is reversed from concentrated solution to less concentrated solution, by a pressure higher than osmotic pressure. A reverse osmosis membrane passes water and small non-ionized (or non-charged) molecules easily through due to the small molecular size and higher water diffusion, but will stop many other contaminants.

Membrane

A semipermeable membrane used in reverse osmosis systems and may consist of a thin film of polymeric material, usually polyamide, cast on a fabric support. The membrane must have high water permeability and ion rejection. The rate of water transport must be much higher than the rate of transport of dissolved ions. The membrane must be stable over a wide range of pH and temperature and have good mechanical integrity.

Spacer

A mesh-like layer situated on top of, essentially parallel to at a constant distance from a surface. The spacer may be made of connected strands of metal, fiber, or other flexible/ductile materials.

Deposit Formation

Deposit formation may consist of scaling, by which in literature is usually meant inorganic fouling by inorganic matter. The deposit may also consist of organic fouling, which is similar but the deposit consist of mainly organic material. Biofouling, microbiological fouling or biological fouling, is a deposit caused by the accumulation of microorganisms, plants, algae, or animals on wetted surfaces. A fouling that involves more than one foulant or more than one fouling mechanism https://en.wikipedia.org/wiki/Fouling—cite note-11 working simultaneously is referred to as composite fouling. Multiple foulants or mechanisms may interact with each other resulting in a synergistic fouling which is not a simple arithmetic sum of the individual components.

It is thus an object of the present invention to present an improved method and apparatus for monitoring and controlling scaling and/or fouling in filtration processes.

SUMMARY OF THE INVENTION

In a method according to the present invention for monitoring deposit formation in a process comprising an aqueous flow a feed flow of an aqueous liquid is provided onto a receiving surface to be monitored. The monitoring method includes the steps of:

illuminating at least part of said receiving surface with at least one light source;

collecting visual data at a multitude of positions across said receiving surface;

analyzing said visual data;

classifying the quality and type of deposition attached to said receiving surface based on information obtained from said analyzed visual data; and computing a quantitative scaling and/or fouling indication of said receiving surface based on said classification.

In short, an aqueous flow is conducted to a measuring cell, where automatic imaging the measuring cell takes place simultaneously with appropriate illumination of cell. The imaging data is processed, classification of fouling types is carried out, and key variables for the fouling, such as fouling level and fouling rate for each fouling type, are calculated. The calculated variables may be used to determine appropriate measures to be taken against the depositions, specifically for optimizing chemical treatment programs, including parameters like the type and dosage of anti-deposition chemicals to be added, the combination (recipe) of such chemicals, and the choice of dosing points, if available.

The collected visual data from the multitude of positions may, as a matter of design choice, be combined into an image representative of said receiving surface before the analyzing step, or the images may be analyzed individually and the information they contain may be combined to gain an understanding of the depositions on the whole receiving surface. The classification of the quality and type of depositions may be done in a computer by using shape factors such as aspect ratio, size factors such as size distribution or mean size, color factors such as mean color, color distribution and brightness, of the depositions imaged.

The quantitative scaling and/or fouling indication of a receiving surface may be based on one or more of the following: total fouling of said surface, fouling rate, a color map of fouling, share or ratio of each fouling type out of a total fouling value. The fouling variables may, for example, be based on local fouling values, fouling maps over a receiving surface, or a cumulated total fouling value.

In some embodiments, computing of the quantitative indication of depositions is based on said classification and used as an input parameter for automatic control of the addition of chemicals to the feed flow. The chemical may be selected from the group of antiscalant, biocides, coagulant chemicals, oxidants, or a polymer.

In some embodiments, at least one of the light sources is an ultraviolet light source and/or a light source which includes a selected wavelength that produces fluorescence in the illuminated target. In some embodiments, it is then possible to classify the quality and type of biofouling deposition involving microbes by adding to a feed flow of aqueous liquid fluorescent dyes capable of staining the microbes, and then by alternately illuminating the deposits on a surface with two light sources, one of which use white light and the other use light with a selected wavelength that excites the fluorescent dye. Ultraviolet light may also cause inherent fluorescence (auto-fluorescence) in the deposits, without any addition of dyes.

In some embodiments, the receiving surface to be monitored is located in at least one monitoring cell having at least one inlet for said feed flow of an aqueous liquid and at least one outlet for a discharge flow from said monitoring cell. The feed flow of an aqueous liquid is introduced onto the receiving surface of the monitoring cell, which in some embodiments may include at least one layer of a spacer applied above said surface. The visual data may then be collected both from the spacer and the receiving surface. Spacers are well known in the art and are used for distributing and moderating the liquid over a membrane.

In some embodiments, the receiving surface may be impermeable. An impermeable receiving surface can be a solid surface like steel/metal or plastic simulating industrial processes.

In some embodiments, the receiving surface may be a semipermeable membrane. A semipermeable membrane produces a permeate part that is passing through said semipermeable membrane and a concentrate part that forms a discharge flow. The semipermeable membrane may be a reverse osmosis, nanofiltration, ultrafiltration or a microfiltration semipermeable membrane.

According to one aspect of the inventive method, at least two monitoring cells are provided, which are monitored by connecting them in parallel with regard to the feed and discharge flows and visual data is collected from the surfaces all monitoring cells.

Various embodiments of the invention may be used in any water-intensive process. For example, the process may be a filtration process, and it can be a reverse osmosis, nanofiltration, ultrafiltration or microfiltration process for treating salt water, e.g. sea or brackish water, or a filtration process for circulated or waste water, or a filtration process for industrial process water, such as paper mill process water. It can be used also in water stream systems, such as in internal water circulation and in raw/waste water treatments, in pulp & paper mills or in oil and mining industry, as well as in other water intensive processes, such as cooling water circulation systems.

According to one aspect of the invention, an apparatus for monitoring deposit formation in a process comprising an aqueous flow is provided. The inventive apparatus comprises:

at least one feed inlet for said aqueous flow onto a receiving surface to be monitored;

at least one light source adapted to illuminate at least part of said receiving surface;

an imaging device arranged to be moved across said receiving surface to collect visual data at a multitude of positions across said surface;

a data processing unit adapted to analyze said collected visual data;

a classifying algorithm for classifying the quality and type of deposition attached to said receiving surface based on information obtained from said analyzed visual data; and a computer routine for computing a quantitative scaling and/or fouling indication of said receiving surface based on said classification.

In some embodiments, the inventive apparatus includes means for adding at least one fluorescent dye to the feed flow of an aqueous liquid. At least two light sources are used for illumination, one of which uses light with a selected wavelength that excites the used fluorescent dye. The classifying algorithm need then be configured to classify the quality and type of biofouling deposition on said receiving surface based on fluorescence emission from the depositions in the analyzed visual data. However, as mentioned above, ultraviolet light may also cause inherent fluorescence (auto-fluorescence) in the deposits, without any addition of dyes.

According to some embodiments, the computing of a quantitative indication of the depositions on the receiving surface is based on the classification as compared to a corresponding clean surface used as a monitoring reference, and is used as an input parameter for automatic control of a chemical dosing to the feed flow. The chemical dosing may include dosing of a chemical that is selected from the group of antiscalant, biocides, coagulant chemicals, oxidants, or that is a polymer.

The present invention offers a multitude of advantages, including early detection of any fouling or scaling in a membrane process involving a commercial membrane cell. It is based on an image analysis system with 1D/2D scanning, which enables monitoring of the whole monitoring cell surface, and of more than one cell at a time. This increases the amount of representative data, and makes the system less vulnerable for misinterpretation of "selective" scaling and fouling on only part of the membrane or surface. With more image data to process and analyze, it is also easier to filter out errors, slight changes in lighting circumstances, etc. Using both an even membrane surface and a spacer in the monitoring cells provide much more contact surface and local turbulence, which provides for microbe growth and thus also for early detection of biofouling.

The invention also makes it possible to monitor with one system several water lines or the same water line before and after biocide or chemical treatment. With the inventive method and apparatus, classification of fouling or scaling is provided, including inorganic, organic and biofouling. Automatic or manual dosing of chemicals can be reliably based on information of the measured fouling value/level, the rate and its type. Accurate dosing is helped by monitoring two lines: before chemical dosing (early detection of fouling), and after (detecting the chemical response). The classification of the quality of scaling and fouling is preferably done in a computer by using shape factors, colors, brightness and/or size. Shape factors may be the coarseness, roundness and/or aspect ratio of a particle. The classification may involve comparison of acquired image data to a predetermined reference library containing model images of scaling and fouling, and/or to a completely clean monitoring cell.

A computed classification may be used as an input parameter for automatic control of the addition of anti-scaling and/or antifouling chemicals to the feed flow. Such chemicals include performic acid (PFA), which is a peroxide derivative of formic acid that is capable of destroying microbiological cells, and sodium hypochlorite (NaOCl), also called hypo.

A fouling value/level [%] refers to the fouling surface area per total surface area. A fouling rate [%/h] may refer to the change in fouling value. Values can be measured locally in the measuring cell or values can be average values describing e.g. mean value of the whole measuring cell.

Calculated values for total fouling in a measuring cell (membrane or any other surfaces) may include:
  Total fouling value, total fouling rate, color map of fouling, total fouling map of measuring cell (total is the sum parameter of all fouling types)
  Total fouling value and total fouling rate for membrane surface, total fouling value and total fouling rate for spacer (if membrane and spacer are included to measuring cell)

Calculated values for various types of fouling in a measuring cell may include:
  Mean color, aspect ratio, size distribution, color distribution, fouling value, fouling rate, mean size, count of fouling objects, ratio of fouling value from the total fouling value, fouling map, share of each fouling types
  Fouling value and fouling rate for membrane surface, fouling value for spacer (if membrane and spacer are included to measuring cell)

In order to provide a broad range of scaling and fouling detection, the inventive method and process advantageously includes computerized classification of the quality of scaling and fouling on the monitoring cell by evaluating shape, colors or grey scale intensity and/or size of any detected scaling and fouling. The quantity of scaling and fouling on a monitoring cell is determined by comparing the obtained visual information to visual information representative of a clean monitoring cell. Advantageously, the computed scaling and/or fouling indication can be used as an input parameter for dosage control of scaling cleaning and/or antifouling chemicals in the main filtration process.

The use of the invention is versatile, as it can be used in membrane processes such as reverse osmosis, nanofiltration, microfiltration and ultrafiltration for a variety of applications. For example, the inventive concept may find use in desalination of sea water or brackish water, in processes for purifying waste water or circulated water. It can be used also in water stream systems in pulp & paper mills or the mining industry, as well as in other water intensive processes to estimate agglomeration of impurities on a suitable surface of the plant itself or in monitoring cells.

The various advantageous embodiments of the invention are characterized by what is said in the appended claims.

BRIEF DESCRIPTION OF THE DRAWINGS

The invention is in the following described in further detail by making reference to the appended drawings, where.

DETAILED DESCRIPTION OF EMBODIMENTS

As used herein, the term "fouling indication" or "scaling indication" may take a number of forms. It can refer to a contaminated surface area as a percentage of a total surface area. It can also refer to the change in the fouling compared with an earlier observation, or to the rate of change of fouling, e.g. as a percentage/time unit. Moreover, a total fouling value and rate may be computed as a fouling indication of a combination of surfaces, e.g. a membrane and a spacer, if such are both monitored. Furthermore, a fouling indication may be a combined fouling indication consisting of individually measured fouling indications for different fouling types. Finally, a fouling indication may take one or be a composite of several factors, such as the mean color, aspect ratio, size distribution, and/or color distribution of the depositions, the fouling value, fouling rate, mean size, count of fouling objects on a surface, etc.

In FIGS. 1-5 are shown spacers on membranes, each having various kinds of fouling deposits. The spacers are a mesh-like network that is placed on the top of membrane to distribute and control the incoming feed flow. Spacers contribute to the pressure drop across the membrane, which will increase because of deposits, such as scaling and fouling accumulation. Each of the types of fouling is in the following described in more detail by making reference to FIGS. 1-5. It is to be noted that the spacers are not an essential part of the invention, and that also a membrane or any surface where deposits may develop may be monitored with the inventive method and apparatus. For monitoring purposes however, the more contact surfaces there are present in the image field of a monitoring apparatus, the faster a deposit buildup can be discovered and diagnosed, and the appropriate counter-measures planned and executed.

Figure 1:
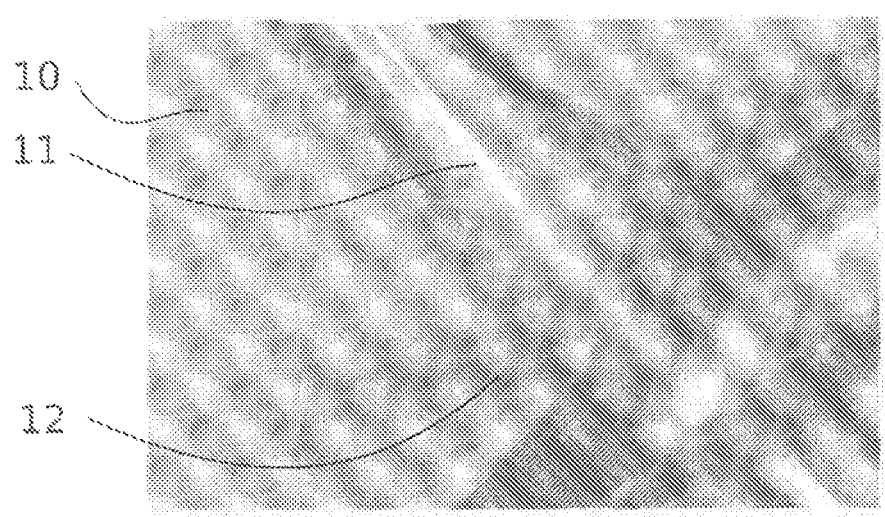
FIG. 1 shows a detail of a spacer on a membrane having a biofouling deposition.

FIG. 1 shows a detailed image of a membrane surface 10, where filaments 12 are attached to a spacer 11. The filaments can clearly be seen by eye, although the outlines of filaments are difficult to recognize. However, with an imaging device such as a digital camera and appropriate image processing software, it is possible to automatically construct the outlines of thin and elongated filaments, e.g. by relying on local image gradients and weight the longitudinal direction of each filament. Such filaments can thus be identified and classified.

Figure 2:
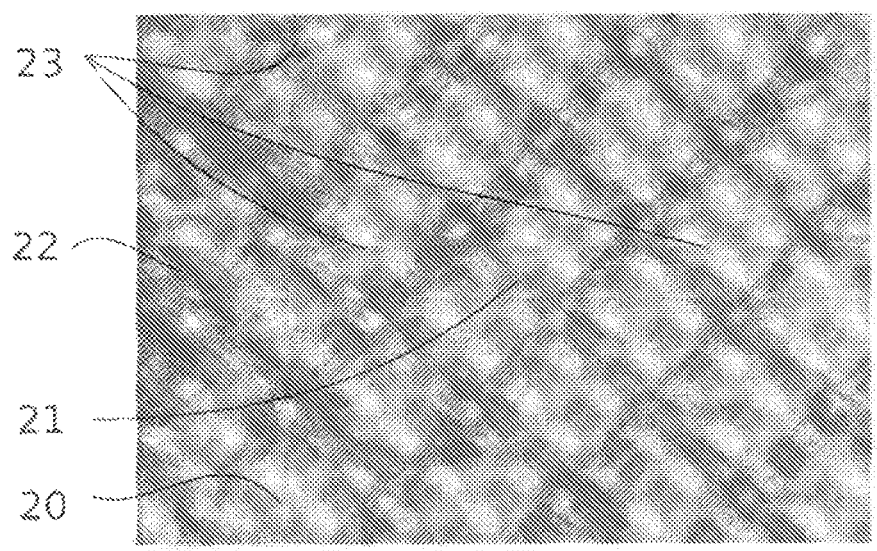
FIG. 2 shows a further example of a spacer with biofouling.

FIG. 2 shows a further example of biofouling on a membrane 20 and a spacer 21. Filaments 22 and black soil 23 particles are shown.

Figure 3:
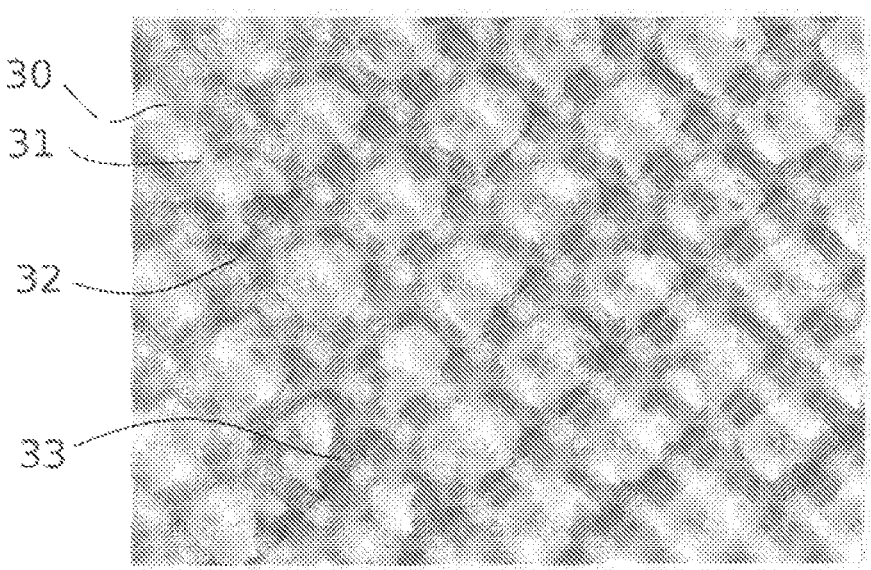
FIG. 3 shows a spacer with both inorganic and organic fouling.

FIG. 3 shows inorganic fouling 31 with grey color mostly deposited on a spacer 31 and organic fouling 33 with brown color mostly found on the membrane 30. Organic fouling has shades of brown and green, which are easily recognized by a color camera and can thus be separated and classified apart from inorganic fouling.

Figure 4:
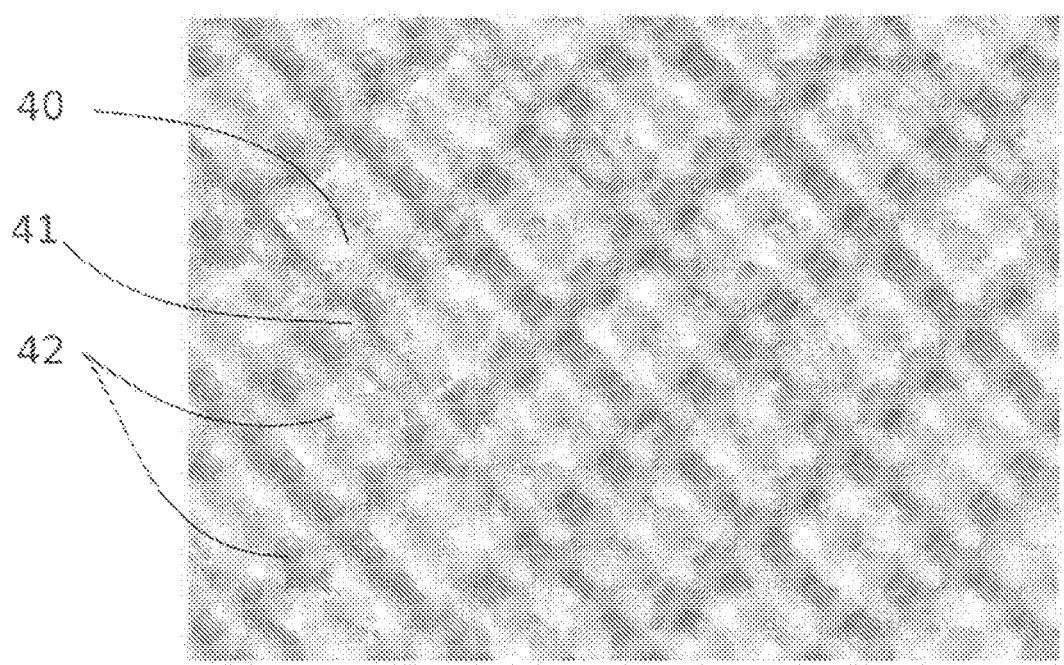
FIGS. 4 and 5 show membranes and spacers with inorganic fouling.
Figure 5:
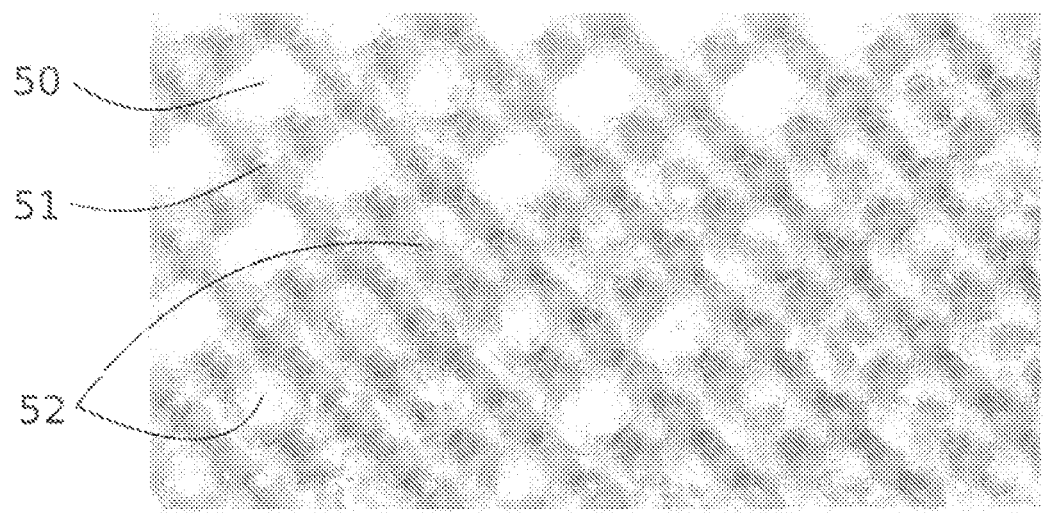

FIGS. 4 and 5 shows membranes 40 and 50 and spacers 41 and 51 with inorganic fouling 42 and 52, respectively. Inorganic fouling such as salt and particles, and gas bubbles appear colorless with shades of grey.

Deposition classification schemes are based on object size, shape, texture and color. Filaments are elongated, thin webs. Fibrous objects have constant width and large length/width-ratio. Micro-bubbles are spherical and their images have bright midpoints. Sand and rocks are fully black. Crystals are bright and they possess straight elements and sharp edges.

Color-based classification schemes may be used to differentiate colorful species from grey, colorless species. The main color of each object may be reported and the colorful species can be further discriminated in color classes, e.g. green and round objects can be classified as algae. Classification methodology and algorithms are explained in detail later on.

Biofouling is dominantly a feed spacer problem, as biofilm accumulation on the feed channel spacer influences the velocity distribution profile. Therefore, biofouling control need low fouling feed spacers and hydrodynamic conditions that restricts the impact of biomass accumulation on the feed channel pressure drop.

In some embodiments, fluorescent dyes may therefore be added to a feed flow of an aqueous liquid, which are capable of staining desired types of microbes. When illuminating biofouling depositions with two different light sources, of which one at least uses light with a selected wavelength that excites a fluorescent dye, it is possible to enhance the classification and identification of biofouling depositions. This is based on fluorescence emissions from the depositions. Microbe staining chemicals may work with different mechanisms depending on the microbes, e.g. through the metabolism of the microbes, and their status (viable, non-viable or dead). For example CTC (tetrazolium salt 5-cyano-2,3-ditolyltetrazolium chloride and DAPI (4',6-diamidino-2-phenylindole) are well-known compositions with microbe staining capability.

The present invention addresses both the problem of the biofouling deposition shown in FIGS. 1 and 2, and the organic and inorganic fouling shown in FIGS. 3-5. Biofouling often represents a more challenging problem than other deposits, and will be discussed in more detail below. Visually biofouling is different from other deposits in that it may become filamentous, as can clearly be seen in FIGS. 1 and 2. Also, compared to smooth nonporous surfaces, membrane biofouling is a complicated process and is affected by many factors, including operating conditions, such as shear and pressure, characteristics of the bacteria themselves, the membrane surface, and environmental factors such as pH, ionic strength, and ion species. Finally, microbial communities are adaptive. Thus environmental pressures (such as chemical or physical stress) will eventually select for organisms that can tolerate those conditions to colonize the surfaces.

Initial bacterial deposition and biofilm development may start on the membrane and develops as a biofilm over time to cover more areas and starts to grow on the spacer. Microorganisms actively colonize over membranes using a broad range of behaviors that can be categorized into a series of defined stages that include: reversible and irreversible attachment (mostly electrokinetic and hydrophobic interaction), movement of reversibly attached cells across the surface and initiation of micro-colony formation, maturation, differentiation and finally biofilm dissolution and dispersal.

Once a membrane surface has become coated in a layer of foulants, subsequent buildup of fouling depends largely on the interaction between the fouled surface and thereto attached foulant. If the suspension is thermodynamically stable, no further absorption will occur, resulting in a relatively small decrease to a stable flux. If, on the other hand, the suspension is unstable, additional layers of fouling will build up, and a sustained decline in flux is observed.

Figure 6A:
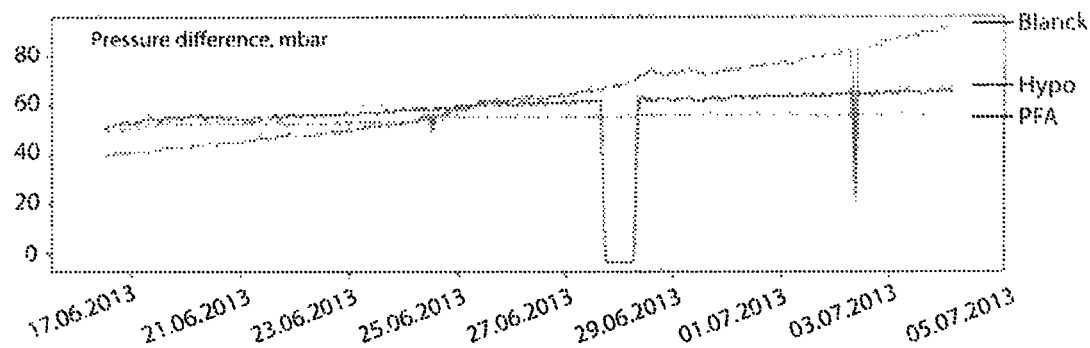
FIGS. 6A, 6B and 6C show characteristic variables for fouling detected with an inventive apparatus.
Figure 6B:
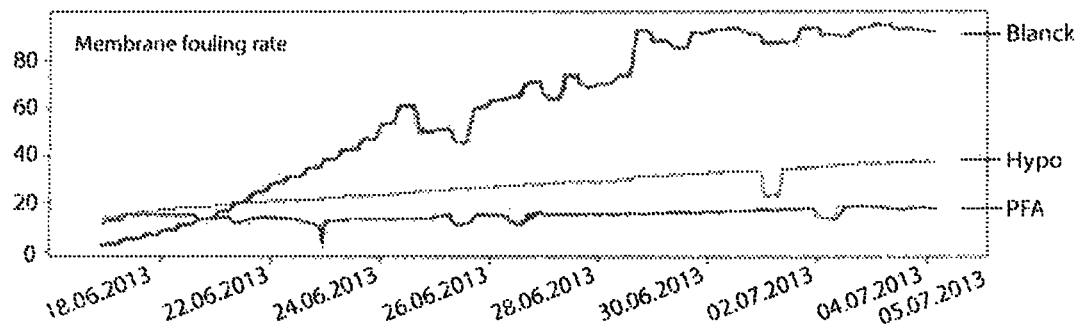
Figure 6C:
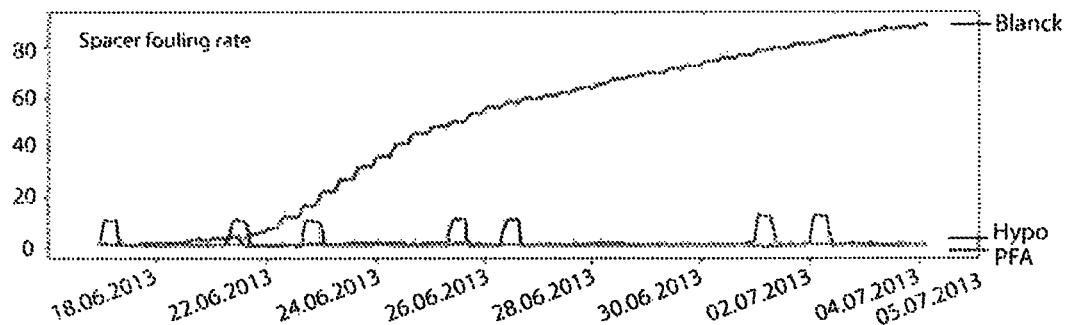

FIGS. 6A, 6B and 6C show characteristic variables for fouling on a membrane and a spacer by real time monitoring of a flow-through cell according to the present invention. The measurement time span is 16 days in all cases.

In FIG. 6A is shown the pressure drop across the cell in three different materials cases, using HYPO (sodium hypochlorite), PFA (a peroxide derivative of formic acid) and no anti-fouling additives (BLANK). As can be seen, the pressure drop steadily increases if no additives are used.

In FIG. 6B, the membrane fouling rate (%) is shown for each case, the BLANK curve indicating that the membrane may easily get totally covered (100% fouling) in a relatively short period of time.

In FIG. 6C, the spacer fouling rate (%) is shown, showing again and clearly the effectiveness of the added chemicals compared to the BLANK curve.

Figure 7:
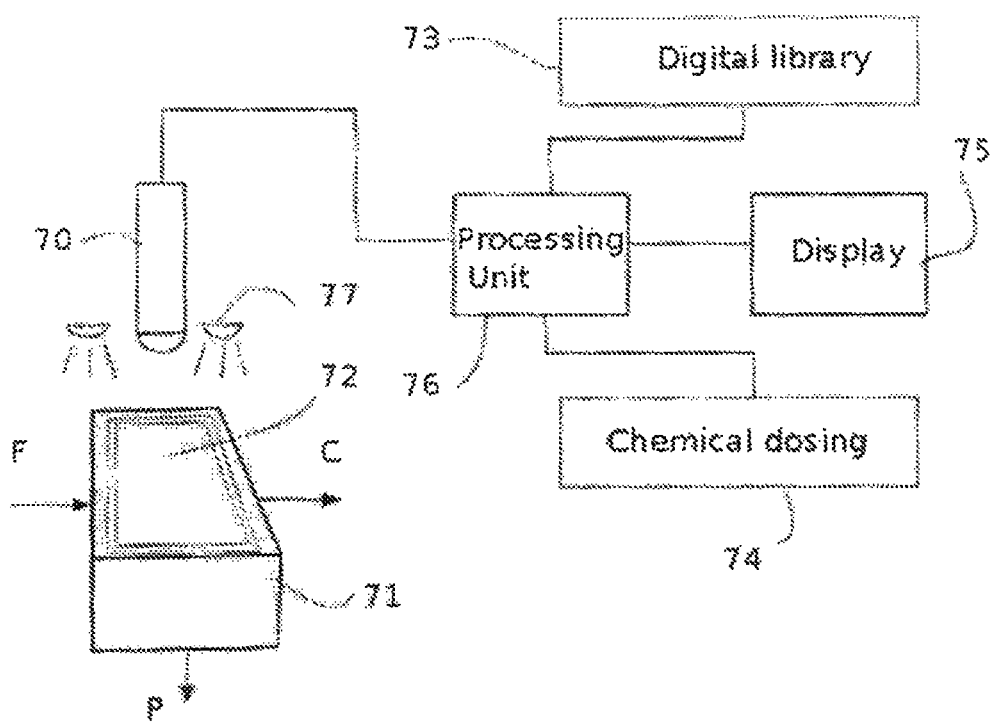
FIG. 7 shows a schematic overall view of the inventive apparatus.

In FIG. 7 is shown a schematic picture of the inventive apparatus. A camera 70 is collecting visual information from the upper surface 72 of, in this embodiment, a reverse osmosis cell 71. The cell 71 is provided with an input feed flow F, an output C for the non-filtered concentrate flow, and another output P for the filtered permeate flow. It is to be noted that the permeate output P is optional, as scaling and fouling deposits can be monitored and analyzed both on surfaces 72 that is impermeable or semipermeable. The scaling and fouling on the surface and the spacer as shown in FIGS. 1-5 will take place anyway.

When having at least one spacer layer applied on the receiving surface, the visual data may then be collected both from the spacer and the receiving surface. This is easy to accomplish either by focusing the lens on the two pictured monitoring cells in turn, or by having a sufficient depth of field in the lens to make both sharp simultaneously.

The camera 70 collects information from the surface 72 as has been described in connection with FIGS. 2 and 3, necessary illumination being provided by lamps 77. The lighting fixture 77 may for example consist of LED lamps or arrays, lasers, Xenon lights or halogen lights. The light may be constant or intermittently flashing (strobe light). The used light may also be of any desired wavelength, in order to best bring the form and features visible to the camera. By using white light, it is possible to get information of the color, brightness, shape and size of the fouling. In some embodiments more than one light source may be used, of which at least one may use ultraviolet (UV) light and/or at least one may use light that produce fluorescence emissions in the illuminated target.

In some embodiments, the inventive method and system may be based on imaging analysis technology and the use of different light sources for illumination, like white light and UV-light, for example. By using UV-light it may be possible to further enhance the type classification of fouling. As at least some organic fouling absorb UV-light, they appears as dark objects in an image taken with UV light. Biofouling again may contain components that produce fluorescence when they are excited by UV or some other light with a suitable wavelength. Such depositions may be seen as bright objects in the images.

In an embodiment, a receiving surface, with or without grids, is illuminated by means of different light sources for illumination with white light and/or UV-light. By using UV-light, biofouling may be identified and measured. By using white light, especially other fouling types may be identified and measured.

Data processing unit 76 analyzes the collected visual data from the receiving surface 72. It also classifies the quality of scaling and fouling on the receiving surface based on information obtained from the visual data and compares it with stored information in a digital library 73. Such a library may comprise a selection of pictures or graphic representations of different scaling and fouling types, to which the visual data is compared and the classification is carried out by using predetermined classification rules/criteria. The library may of course be targeted to cover the specific process or situation in question.

Finally it computes a scaling and/or fouling indication or index which is displayed on display 75 or sent to any other output means for evaluation and, optionally, sends a control signal to a chemical dosing device 74 of a main filtration or other process. It is to be understood that the inventive method and system can operate on a separate feed flow taken out by any means from a main process (not shown).

The processes that can be monitored by the inventive method and apparatus include desalination processes of sea or brackish water, waste water and circulated water, for example. The filtration units may be reverse osmosis membranes, nanofiltration membranes, and ultra- or microfiltration membranes. The usability of the invention is thus not depending on the liquid to be filtered, or the quality or grade of the filter. The inventive method is based on monitoring and comparing, which means some knowledge is assumed on the fouling and scaling that can occur, and how it will build up on the surfaces. Once this knowledge is established, the inventive method and apparatus may be successfully employed.

Figure 8:
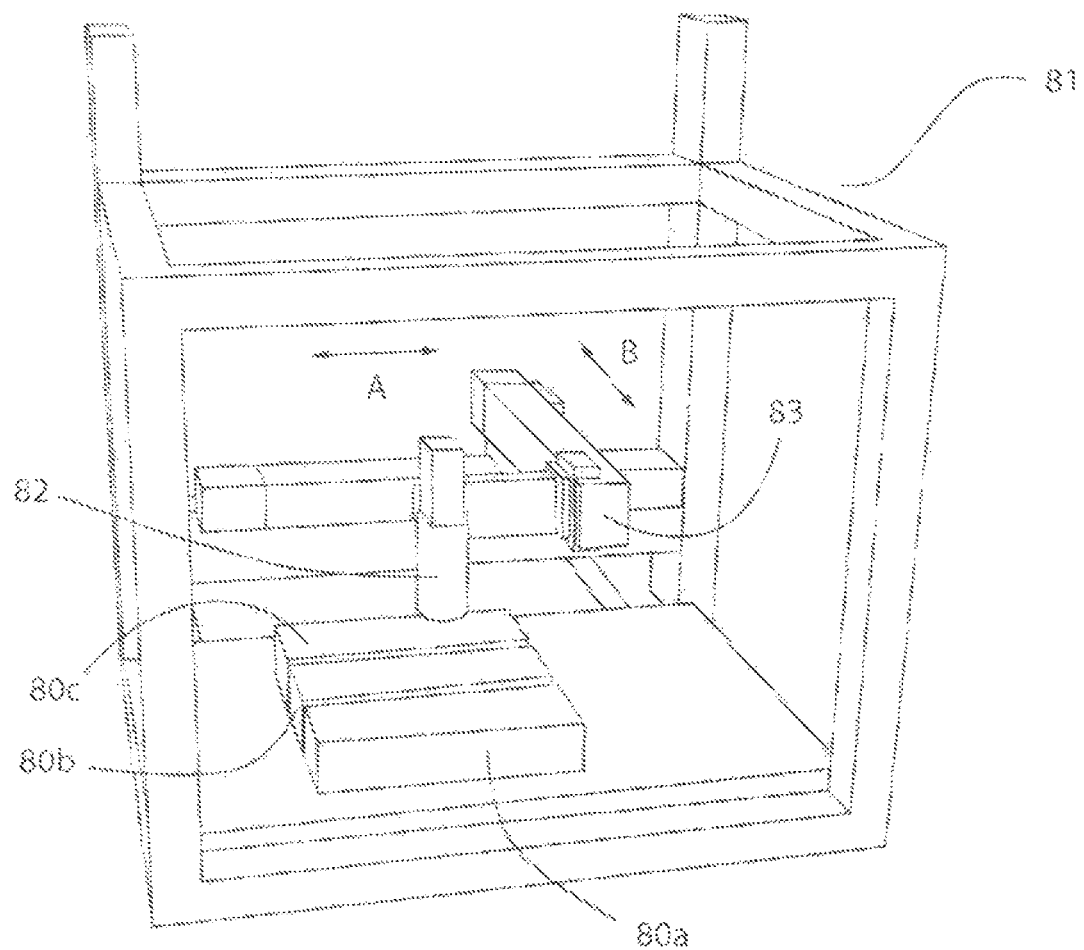
FIG. 8 shows a monitoring unit according to the present invention.

In FIG. 8 is shown an exemplary monitoring unit 81 according to the present invention for monitoring scaling and fouling in a process. It shows three cells 80a, 80b and 80c to be monitored and an imaging device 82 mounted on a framework 83. The framework is arranged to move the imaging device 82 with its illumination devices across cells 80a-80c to be monitored to collect visual across their surfaces. The imaging device 82, preferably a digital CCD camera equipped with a high-magnification lens, can be moved as shown by arrows A and B. Alternatively the camera may be in fixed position over the cells 80a-80c, but being able to picture their upper surfaces by scanning. Preferably, the camera 82 is mounted on a linear guide powered by a stepper motor which moves the camera between multiple imaging locations.

In this example, a camera is used to measure scaling and fouling from three identical separate measuring cells 80a, 80b and 80c. Images from the camera are analyzed with an analysis software running on an industrial PC 104 (see FIG. 10), and the analysis results are transferred to the PLC's 101 data block for data acquisition and visualization on the HMI panel 102.

The cells 80a-80c are connected in parallel to provide a larger sample of the same process step in a filtration plant, but they can also be connected to different flow streams and be used for showing the situation in different steps of the filtration process. This is useful e.g. when studying effects of e.g. added anti-fouling chemicals or changed process parameters.

In one exemplary setup, referring generally to FIGS. 7 and 8, a measuring cell is illuminated with white and UV LED lights, the UV wavelength being 395 nm, for example. A CCD camera and a unit for processing imaging data are also provided.

In a first step, an aqueous flow, in some embodiments containing at least one fluorescent dye, is conducted to the measuring cell. The measuring cell is alternately illuminated with white light, and an UV- or a fluorescent excitation LED light. Visual data is collected from the measuring cell. The imaging and illumination is synchronized, if needed, to produce images by each scan of the camera. The image data is then preprocessed and the fouling types are identified and classified. Black objectives are classified as organic fouling and fluorescence-emitting objects are classified as biofouling. The key variables for the fouling, such as the fouling level and fouling rate for each type is then computed. The computed variables are then used for monitoring and controlling the fouling in water intensive processes, e.g. membrane processes, water streams in industrial processes, such as in pulp and paper mills. The inventive system may be used to calculate chemical dosages and for optimizing chemical programs, including adjustable parameters like recipes of chemicals, their combinations and dosing points.

Figure 9:
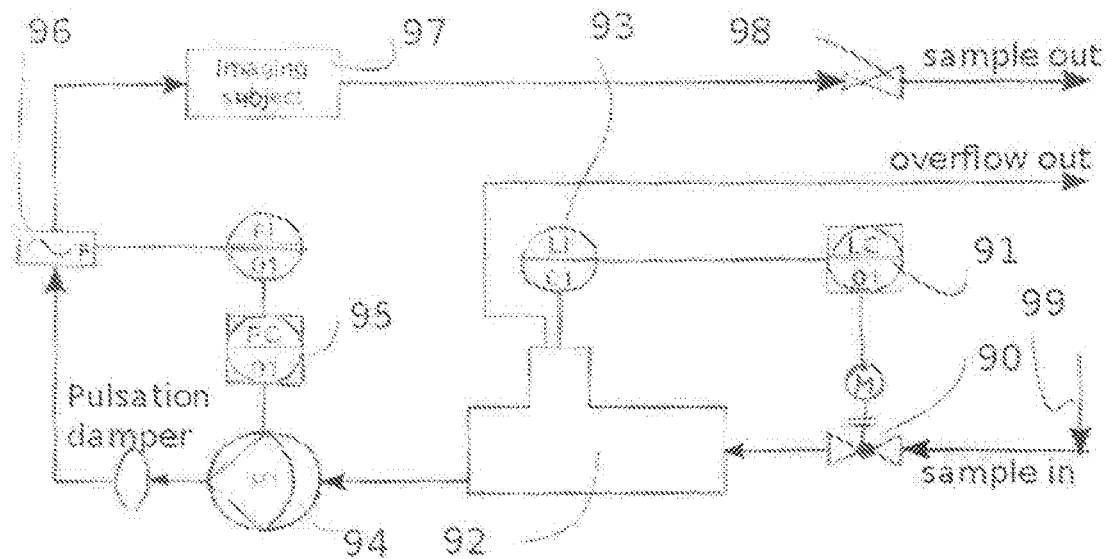
FIG. 9 shows a PI-diagram for a monitoring unit according to the present invention.

In FIG. 9 is shown an exemplary piping and instrumentation (PI) diagram for the monitoring cells 71 of FIG. 7 and cells 80a-80c of FIG. 8. The sample enters through an electrically actuated ball control valve 90 to a sample tank 92. One or several fluorescent dyes may be added to the sample input flow at 99 from an assay or container with a controlled feeding arrangement (not shown). The ball control valve is controlled by a proportional-integralderivative controller (PID controller) 91, which has feedback from an ultrasonic tank liquid level sensor 93. A diaphragm pump 94 controlled by a PID controller 95 taking feedback from an ultrasonic flow meter 96, pumps the sample through the monitoring cell 97 and through a back pressure valve 98 out of the apparatus.

Figure 10:
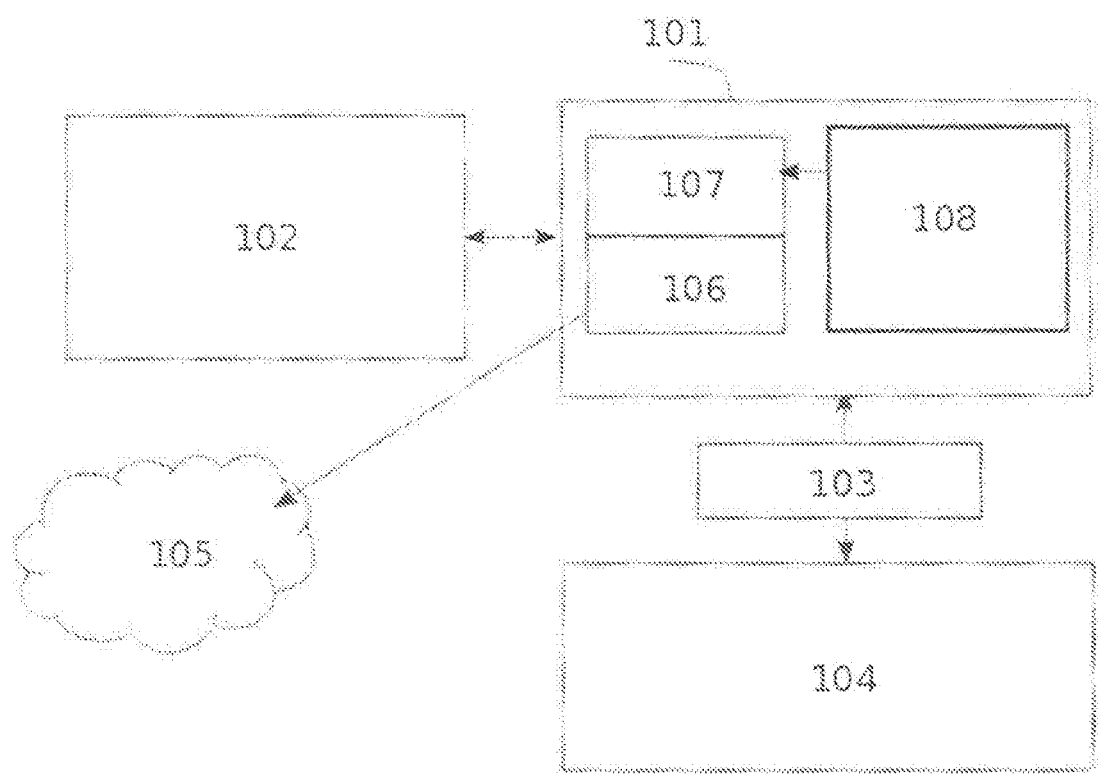
FIG. 10 shows a schematic overview of a data processing unit for a monitoring unit according to the present invention.

In FIG. 10 is shown a schematic overview of an example of a data processing unit that may be used in the inventive apparatus. A programmable logic controller (PLC) 101, for example a Siemens S7-1200 PLC is used to control the operations of the analyzing equipment. An industrial or generalpurpose computer 104 runs the analysis software required for the visual data processing and image rendering. Further main components are a touchscreen interface 102, such as a Human Machine Interface Panel for example, a communication software library 103 and the internet 105.

The communication library 103 may be an Open Data Communications Data Access (OPC DA) client that provides the analysis software running on the computer 104 with synchronous read and write access to the PLC's 101 memory. The analysis software requests a connection from the communication library which then tries to establish the connection to the PLC 101. The connection is then active until the analysis software is closed, and provides access to various PLC memory variables for the analysis software via a multitude of functions.

The PLC program is used to control operations of the exemplary systems laid out in FIGS. 7-9. It has a data block 106 used for online dataacquisition via a router that sends the data to a server on the internet 105. The hardware controller 107 controls e.g. two control valves, two pumps and one linear guide driven by a stepper motor, the camera and a LED ring light for illumination. A control signal to a chemical dosing device 74 of FIG. 7 may be sent over a network 105 or over a dedicated line (not shown) to a valve in practice controlling the chemical dosage to a main process.

The PLC 101 also has a data block 108 which can be accessed symbolically and that contains software modules designed for camera and lighting control.

The touchscreen user interface 102 is used to control the inventive apparatus, to configure the connection settings, set the analysis parameters and to visualize the current status of the analyzer.

Figure 11:
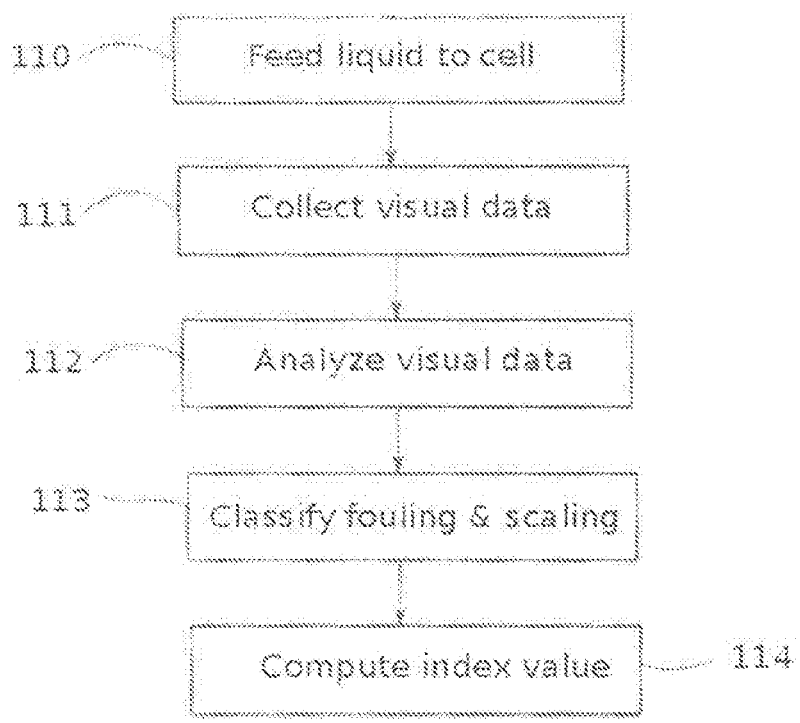
FIG. 11 shows a flowchart of the method according to the present invention.

FIG. 11 depicts a flowchart over the inventive method. In the first step 110, a water feed flow, in some embodiments containing at least one fluorescent dye, is fed to at least one receiving cell, having for example a reverse osmosis (RO) membrane fitted. In the second step 111, a camera support similar to the framework 81 in FIG. 8 is employed to move a camera 82 to cover the surface of the at least one RO cell 80a-80c. The camera is taking pictures, i.e. collecting visual data, at or from predetermined spots of the upper surface of the cells. Having covered the whole area to be monitored in step 111, the collected visual data is analyzed in step 112. Analyzing the data means here processing the data in order to make it comparable with pre-stored visual information about scaling and fouling and comparing the data with pre-stored visual content in a digital library.

Based on the analysis in 112, the type and amount of fouling and scaling can be identified in step 113. In step 114, an indication, index or any predetermined parameter, that is a quantitative and/or qualitative measurement result of the deposits on the RO cell, is computed.

Figure 12A:
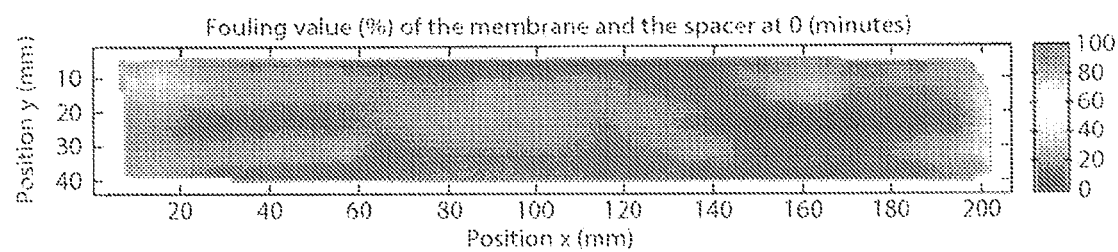
FIGS. 12A and 12B shows a fouling map of a monitoring cell according to the invention.
Figure 12B:
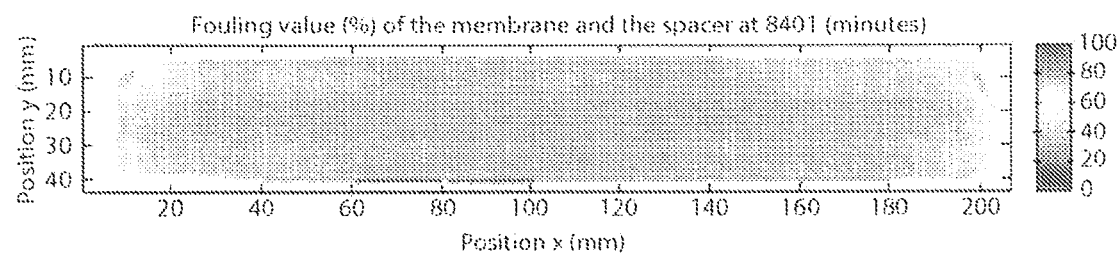

In FIGS. 12A and 12B is shown in practice visual data collected from the receiving surface of a monitoring cell according to the invention. Pictures a and b covers the receiving surface area of the same monitoring cell, and are called "fouling maps". In picture a, no fouling exist, and the fouling map has a deep blue color (here dark grey). In picture b, taken after one week of aqueous flow through the monitoring cell, the color is distinctly different, now turquoise (here light grey). Fouling has clearly commenced. A fouling value and a fouling rate, may therefore be calculated as described above.

As an example of deposition classification, a Bayesian—Laplace probabilistic classification approach is used, which is robust and well suited to discriminate different species of deposits from each other. As a rule, all objects should be classified to one specific object or particle class, like filaments, deposits of crystals, scales and other fouling objects. The classification may also rely on a hypercube approach, which means that a particle is classified to a particle class when particle's every property remains between the discrete minimum and maximum limits specified for the class.

Classification of Objects

In the following, an exemplary sequence of steps to classify an object, i.e. a deposit that has been imaged on a receiving surface is described. A classification scheme may include the phases 1-3 of:

1) Image Filtering

Image filtering is utilized to remove noise, to fade out an unequal background, to highlight the focused objects, and to compute e.g. local greyscale gradient values and their direction. A filtered image may then be equalized e.g. by multi-resolution analysis, e.g. using a Gaussian multiresolution pyramid. A Laplacian image (which is the second derivative of image greyscales) may then be computed from an equalized image to highlight the regions of the greatest greyscale variance.

2) Image Segmentation

The purpose of an image segmentation step is to recognize focused objects in an image and to compute the projective areas and outlines of the objects, and to recognize different types of objects in such image.

Dark regions are recognized by applying a greyscale percentile threshold to a cumulative greyscale histogram of an equalized image. The background of an image may be computed as the mean image of the previous 10 images. Thus structural components of the area to be monitored, like spacers, may be digitally masked at an early stage from the segmentation analysis of the image.

Deposits, i.e. stagnant objects that are slowly building up, are identified from the image using the above mentioned greyscale percentile threshold. The total area of the deposited objects per total image area ×100% may be used as an indicator of a current fouling value.

Focus discrimination on a Laplacian image may be used to validate objects. Objects which projected area has more focused pixels relative to the total area than a user-specified focus ratio (e.g. 7%), are recognized as valid. Regions of high greyscale variance may be highlighted by combining Laplacian, gradient and high-pass filtered images. A binary image of the objects is obtained by applying to the combined image a user-specified contrast threshold and by superimposing on the image the dark regions.

3) Object Morphology

A binary image of an object may be processed with morphological operations. As the projective area of each object is imaged by the camera, the object diameter d is defined based on the object's projective area A as:

$$d = 2 \cdot \sqrt{\frac{A}{\pi}} \quad (5)$$

The morphology of objects may further be studied by defining their shape properties, including the aspect ratio, roundness, and coarseness.

When an object is recognized as an elongated object, an analysis may be carried out to obtain the length and width of the object. An analysis algorithm may be used, where the object length may be computed as the length of the outline (perimeter) divided by two. The width computation may be based on outline vectors consisting of the x,y-coordinates and the greyscale gradient direction value [−π, π] of each outline pixel. A matching point at the opposite side of the image outline is searched by comparing the direction values of the opposite outline pixels and of a line drawn between the matching pixels. The distance between the opposite pixels corresponds to the local width of a object, the overall width of which may then be computed as the mean of all local widths.

The principal axes and aspect ratio of deposits may be computed from the object by using principal component analysis (PCA) algorithm. The algorithm returns the major and minor axes of the object and their orientation angle. The aspect ratio may be computed as simply the ratio between the major and minor axes of the object.

Roundness describes how close to a circle an object is. A perfect circle has a roundness of 100%. The roundness percentage decreases with an increasing complexity of the particle shape. Roundness R is computed as:

$$R = \left(1 - \frac{\sqrt{\frac{\sum_{i}^{N}(r_i - r)^2}{N-1}}}{r}\right) \cdot 100\% \quad (6)$$

where r is the object radius and $r_i = \sqrt{(x_i - x_c)^2 + (y_i - y_c)^2}$ are the distances from outline pixels $(x_i, y_i)$ to the centre point of the object $(x_c, y_c)$. N=perimeter length.

The normalization is obtained by dividing the standard deviation of radii with the object radius.

The coarseness of an object may be computed as the sum of discrete curvatures along the outline of the object divided by the length of the outline. Curvature values may be computed as a difference between the greyscale gradient direction angles of neighboring outline pixels. Only rapid turns in the curvature are counted in the coarseness computation. The coarseness value may be normalized with the perimeter value of a circle having the same diameter as the maximum distance across the object. Kurtosis can be calculated by using $4^{th}$ momentum of grey scale intensity. This can be used for can be used for classification of fouling type.

All detected objects in the receiving surfaces are classified to a one specific fouling type (e.g. biofouling, organic fouling and inorganic fouling or their combination(s)) according to predetermined classification criteria. Classification criteria may also include colors detectable from deposits by using white, ultraviolet or fluorescence excitation light, alone or in combination.

The texture of an object is important for cognitive recognition. Texture analysis may be done by modelling the object texture by studying the brightness (i.e. greyscale intensity) profile from the object center point to its outline. The mean brightness values are computed at the particle center, at the particle outline and at the full particle area. Also the standard deviation of particle's brightness values is computed. The mean brightness values may be utilized to discriminate particles to bright and dark classes and to classify bright and thin objects.

Application Areas

Important examples of application areas are to be found in the paper industry and its water streams. Other examples are oil, mining or water treatment processes, in particular desalination processes, membrane processes, cooling water treatment, and water reuse. Specifically in the paper industry, the subjects for monitoring efforts are organic, inorganic and biofouling, and combinations thereof.

The invention may be used both for monitor and control of the water-intensive processes involved, and thus to control the addition rate of one or more process chemicals. Controlling can be carried out manually, semiautomatically or automatically based on the scaling/fouling analysis carried out according to the invention.

In the method, visual data may be collected at a multitude of positions across a receiving surface, and the visual data is analyzed and classified to determine the quality and type of deposition attached to the receiving surface. In the method it is possible to recognize and classify different fouling types. Fouling type may be inorganic, organic or biofouling. The used deposition classification schemes may be based on object size, shape, texture and color. The method enables measuring the properties of several fouling deposits. It discloses how to identify and classify several different fouling deposits, and enables detecting multiple foulants and classification of foulants attached to the same receiving surface. In the method, actual deposits of all kinds may be monitored, classified and reported. These deposits may include organic, inorganic, and/or biofouling.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A method for monitoring deposit formation in a process involving an aqueous flow, said method comprising:
   providing a feed flow of an aqueous liquid onto a receiving surface to be monitored, wherein the monitoring includes:
   illuminating at least part of said receiving surface with at least one light source;
   collecting, in an imaging device, visual data at a multitude of positions across said receiving surface, wherein the imaging device is moved across said receiving surface to collect said visual data at said multitude of imaging locations across said receiving surface;
   analyzing said visual data;
   classifying a quality and type of deposition attached to said receiving surface based on a comparison of information obtained from said analyzed visual data to stored visual reference data; and
   computing a quantitative scaling and/or fouling indication of said receiving surface based on said classification,
   wherein the classification of the quality and type of said depositions on said receiving surface is done in a computer by comparing the obtained visual data to the stored visual reference data of shape factors that include aspect ratio, size factors that include size distribution or mean size; and color factors that include mean color, color distribution and brightness, of the depositions imaged,
   wherein said quantitative indication of said deposition on said receiving surface, compared to a dean surface used as a reference, is used as an input parameter for automatic control of the addition of one or more chemicals to said feed flow, and
   wherein said receiving surface is a mesh-like network placed on too of a membrane to distribute and control the incoming feed flow.

2. A method according to claim 1, wherein the method comprises:
   classifying a quality and type of biofouling deposition on said receiving surface based on fluorescence emission from said depositions in said analyzed visual data.

3. A method according to claim 1, wherein at least one of said light sources is emitting ultraviolet light.

4. A method according to claim 1, wherein the quantitative scaling and/or fouling indication of said receiving surface is further based on one or more of the following: total fouling of said surface, fouling rate, color map of fouling, and/or share or ratio of each fouling type.

5. A method according to claim 1, wherein said receiving surface to be monitored is located in at least one monitoring cell having at least one inlet for said feed flow of an aqueous liquid and at least one outlet for a discharge flow from said monitoring cell.

6. A method according to claim 5, comprising:
   introducing said feed flow of aqueous liquid onto a receiving surface of said monitoring cell including at least one layer of a spacer applied on said surface.

7. A method according to claim 6, wherein said visual data is collected from said spacer and said receiving surface.

8. A method according to claim 5, wherein the monitoring cell has a receiving surface that is impermeable.

9. A method according to claim 5, wherein the monitoring cell has a receiving surface that is a semipermeable membrane.

10. A method according to claim 9, wherein said semipermeable membrane produces from said feed flow a permeate part that is passing through said semipermeable membrane and a concentrate part that forms said discharge flow.

11. A method according to claim 9, wherein said semipermeable membrane includes a reverse osmosis, nanofiltration, ultrafiltration or a microfiltration semipermeable membrane.

12. A method according to claim 5, comprising:
    providing at least two monitoring cells to be monitored;
    connecting said monitoring cells in parallel with regard to the feed and discharge flows; and
    collecting visual data of the surfaces of said at least two monitoring cells.

13. A method according to claim 1, wherein said process is a filtration process and is a reverse osmosis, nanofiltration, ultrafiltration or microfiltration process for treating at least one of the following: saline water, brackish water, circulated water, waste water, or industrial process water.

14. A method according to claim 1, wherein said one or more chemicals is selected from the group of antiscalants, biocides, coagulant chemicals, oxidants, cleaning chemicals, polymers and/or any combination thereof.

15. An apparatus for monitoring deposit formation in a process having an aqueous flow, the apparatus comprising:
    at least one feed inlet for directing an aqueous flow onto a receiving surface to be monitored;
    at least one light source arranged to illuminate at least part of said receiving surface;
    an imaging device mounted on a linear guide and arranged to be moved across said receiving surface by a stepper motor to collect visual data at a multitude of positions across said receiving surface;
    a data processing unit configured to analyze said collected visual data;
    a classifying algorithm for classifying quality and type of deposition attached to said receiving surface based on a comparison of information obtained from said analyzed visual data to stored visual reference data; and
    a computer routine for computing a quantitative scaling and/or fouling indication of said receiving surface based on said classification,
    wherein the classification of the quality and type of said depositions on said receiving surface is done in a computer by comparing the obtained visual data to the stored visual reference data of shape factors that include aspect ratio, size factors that include size distribution or mean size, and color factors that include mean color, color distribution and brightness; of the depositions imaged;

wherein said quantitative indication of said deposition on said receiving surface, compared to a clean surface used as a reference, is usable as an input parameter for automatic control of the addition of one or more chemicals to said feed flow, wherein said receiving surface is a mesh-like network placed on top of a membrane to distribute and control the incoming feed flow.

16. An apparatus according to claim 15, comprising:

means for adding at least one fluorescent dye to a feed flow of an aqueous liquid; and at least two light sources, at least one of which uses light with a selected wavelength that excites a biofouling deposit stained by said at least one fluorescent dye;

said classifying algorithm being configured to classify a qualify and type of biofouling deposition on said receiving surface based on fluorescence emission from a deposition in said analyzed visual data.

17. An apparatus according to claim 15, wherein at least one of said light sources is an ultraviolet light source.

18. An apparatus according to claim 15, wherein said data processing unit comprises:

means for computing the quantitative scaling and/or fouling indication of said receiving surface based on one or more of the following: total fouling of said surface, fouling rate, color map of fouling, and/or share or ratio of each fouling type.

19. An apparatus according to claim 15, wherein said receiving surface to be monitored is located in at least one monitoring cell, said monitoring cell having at least one inlet for said feed flow of an aqueous liquid and at least one outlet for a discharge flow from said monitoring cell.

20. An apparatus according to claim 19, wherein said monitoring cell comprises:

at least one spacer layer applied on said receiving surface.

21. An apparatus according to claim 20, wherein said imaging device is arranged to collect visual data from said spacer layer said receiving surface.

22. An apparatus according to claim 19, wherein the monitoring cell comprises:

a receiving surface that is impermeable.

23. An apparatus according to claim 19, wherein the monitoring cell comprises:

a receiving surface that is a semipermeable membrane.

24. An apparatus according to claim 23, wherein said monitoring cell comprises:

an outlet flow for a permeate part that is to pass through said semipermeable membrane, and a discharge outlet for a concentrate part that is not to pass through said semipermeable membrane.

25. An apparatus according to claim 19, comprising:

at least two monitoring cells connected in parallel with regard to their feed and discharge flows, said imaging device being arranged to collect visual data of the receiving surfaces of said at least two monitoring cells.

26. An apparatus according to claim 15, wherein said chemical dosing comprises:

a dosing of a chemical that is selected from the group of antiscalants, biocides, coagulant chemicals, cleaning chemicals polymers and/or any combination thereof.

27. An apparatus according to claim 15, in combination with a process plant to estimate agglomeration of impurities on a receiving surface of said plant.

28. An apparatus according to claim 19 in combination with a filtration process pant, to estimate agglomeration of impurities in monitoring cells of said plant.

* * * * *